United States Patent [19]

Eda et al.

[11] Patent Number: 4,883,752

[45] Date of Patent: Nov. 28, 1989

[54] METHOD FOR PREPARING MONOCLONAL ANTIBODY TO HBSAG

[75] Inventors: Yasuyuki Eda; Toshihiro Maeda; Kiyoto Nishiyama; Akira Tashiro, all of Kumamoto, Japan

[73] Assignee: Juridical Foundation the Chemo-Sero-Therapeutic Research Institute, Kumamoto, Japan

[21] Appl. No.: 791,163

[22] Filed: Oct. 24, 1985

[30] Foreign Application Priority Data

Oct. 26, 1984 [JP] Japan .................. 59-226394

[51] Int. Cl.$^4$ .................. C12P 21/00; C12N 5/00
[52] U.S. Cl. .................. 435/68; 435/240.27; 935/90; 935/100
[58] Field of Search ........... 435/68, 70, 172.2, 240.27; 935/100, 90

[56] References Cited

U.S. PATENT DOCUMENTS 4,271,145  6/1981  Wands et al. .................. 424/85
4,689,299  8/1987  Insel et al. .................. 435/240.27

FOREIGN PATENT DOCUMENTS 0038642 10/1981  European Pat. Off. .
5872526  4/1983  Japan .
2000186  1/1979  United Kingdom .

OTHER PUBLICATIONS

Ichimori, Y. et al., Biochem, Biophys. Res. Comm. 129, (1), 26–33, 1985.
"Continuous cultures of fused cells secreting antibody of predefined specificity", by G. Kohler et al., Nature, Vol. 256, 1975, pp. 495–497.
"Fusion Between Immunoglobulin-Secreting and Nonsecreting Myeloma Cell Lines", by G. Kohler et al., Eur. J. Immunol., Vol. 6, 1976, pp. 292–295.

Primary Examiner—Christine M. Nucker
Assistant Examiner—Karen I. Krupen
Attorney, Agent, or Firm—Fleit, Jacobson, Cohn, Price, Holman & Stern

[57] ABSTRACT

Disclosed is a monoclonal antibody to HBsAg which is prepared by forming hybridomas between human peripheral blood lymphocyte cells, derived from humans having high titers of anti-HBsAg, and myeloma cells, cloning the hybridomas and selecting the antibody-producing clones. The monoclonal antibody can react with all the subtypes of HBsAg and is expected to be very effective in diagnosis and treatment of diseases due to the viral infection.

8 Claims, 2 Drawing Sheets

METHOD FOR PREPARING MONOCLONAL ANTIBODY TO HBSAG

BACKGROUND OF THE INVENTION

The present invention relates to monoclonal antibody, particularly, to human-derived monoclonal antibody to hepatitis B surface antigen (HBsAg).

Hepatitis B virus is a horrible infectious virus causing hepatic insufficiency and chronic hepatitis as well as acute hepatitis, which may develop to liver cirrhosis or liver cancer. Thus, early establishment of diagnosis and treatment of the diseases is being desired.

There are known three types of antibodies to hepatitis B virus: Antibody to the virus surface antigen (HBsAg), antibody to the virus core antigen (HBcAg) and antibody to e antigen which is said to be contained within the core antigen(HBeAg). It has been recently confirmed that the antibody to HBsAg possesses neutralizing activity against hepatitis B virus and is now expected to serve as a reagent to prevent and treat the viral infection. Thus, medical preparations containing anti-HBsAg antibody has attracted a good deal of attention, and attempts have been made to produce the preparations from human plasmas which are positive with respect to antibody to HBsAg. However, such methods are disadvantageous in that there are limitations of supply of human plasmas as raw materials so that the preparations are costly. An object of the invention is to overcome and solve such problem.

PRIOR ART

It is known that the cell fusion technique makes it possible to produce homogeneous or monoclonal antibodies to certain virus antigens. For example, there is disclosed in Japanese patent publication No. 2276/1984 a method for preparing an anti-virus monoclonal antibody which comprises providing fused cell hybrids between anti-virus-antibody-producing cells found in spleens or lymph nodes in mice and myeloma cells, culturing the hybrids and collecting the antibody. However, the disclosed method is directed antibodies influenza virus rabies virus. Further the hybridomas disclosed in this patent application are mouse/mouse hybrid cells formed by fusing antibody-producing spleen cells from mice immunized with the virus antigen and BALB/c myeloma cells derived from the MOPC-21 line. Thus, the monoclonal antibodies produced are mouse-originated ones which give no guarantee whether they can be administered into humans without providing doubt about safety.

Japanese Laid-Open patent application No. 58718/1981 discloses an anti-HBsAg monoclonal antibody, which is also produced from a hybridoma of mouse/mouse fused cells. There is left a doubt whether such antibody can be utilized to diagnose or treat hepatitis viral infections in humans. There is found in Japanese Laid-Open patent application No. 72526/1983 production of a human-based or human-derived monoclonal antibody against HBsAg, where human B lymphoid cells are stimulated by immunization with HBs antigen which has been heated in the presence of a modifier such as urea or guanidine, and transformed to propagatable cells by Epstein-Barr Virus. However, in the patent application no definite disclosures are made on characteristics of such human-derived anti-HBsAg monoclonal antibody.

SUMMARY OF THE INVENTION

After extensive studies to overcome the disadvantages in the conventional techniques, the present inventors have succeeded in producing and characterizing a human-derived anti-HBsAg monoclonal antibody (hereinafter sometimes referred to as hHBs MCA) which can be successfully utilized in diagnosis and treatment of hepatic diseases in humans. Thus, according to the present invention the hHBs MCA can be prepared stably and continuously, by forming hybridomas by means of the cell fusion of human peripheral blood lymphocyte cells, immunized with HBs antigen to a certain degree, and myeloma cells, cloning the hybridomas and selecting clones which produce antibodies to HBsAg.

The hHBs MCA of the present invention is in no way in danger of contaminated with hepatitis B virus since it is derived from the hybridoma. The hybridomas, if once established, can be stored for a long time under liquid nitrogen and utilized for the production on a large-scale of the hHBs MCA by being propagated at any time when needed, without restriction, of the supply of raw materials. The process for purifying the MCA is relatively simple, which will also contribute to the less expensive production of the monoclonal antibody (MCA). The MCA of the present invention is also characterized in that it has an extremely higher specificity for HBsAg as compared with the anti-HBsAg antibodies obtained from the plasmas. Moreover, the administration in human in vivo of the MCA of the invention which is based on human-origin, does not cause side effects as would be encountered in the mouse/mouse anti-HBsAg monoclonal antibodies.

The human-based MCA and the method for preparing the same according to the present invention will be described in more detail in the following.

DETAILED DESCRIPTION OF THE INVENTION

Figure 1:
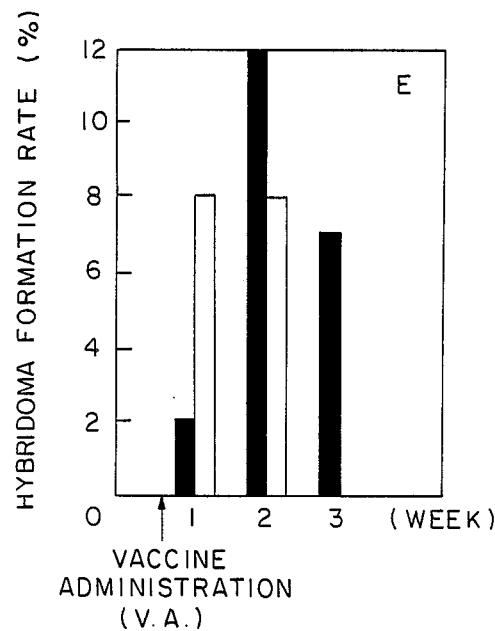
Figure 1:
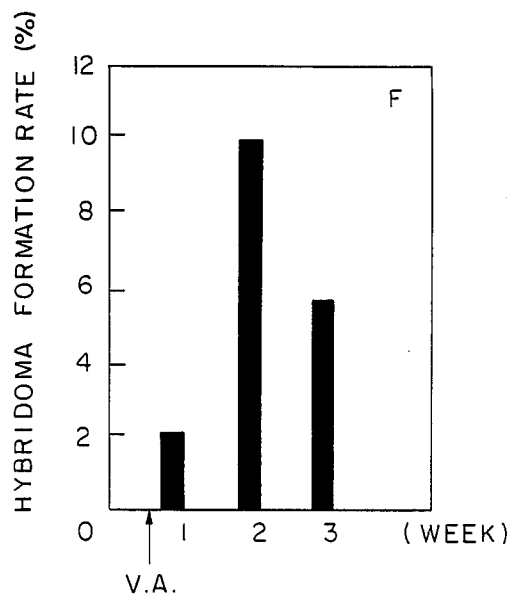
Figure 1:
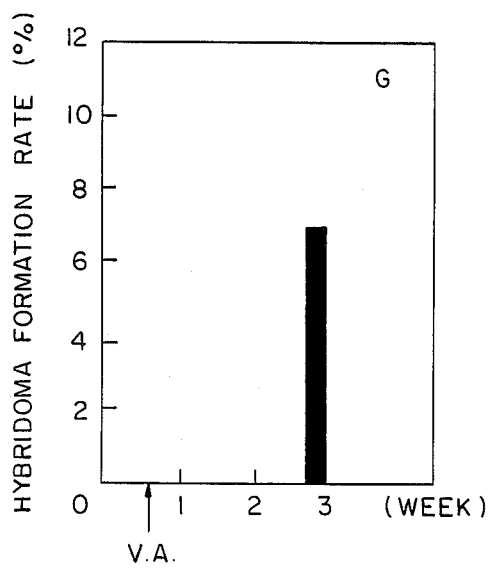
Figure 1:
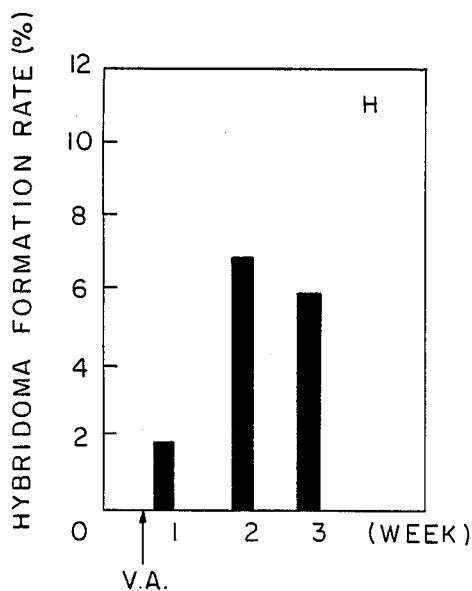

For the production of an anti-HBsAg monoclonal antibody which is compatible to humans, the present invention is directed to the formation of hybridomas of fused mouse/human cells.

The human cells used are peripheral human blood lymphocyte cells derived from humans who are positive with respect to anti-HBsAg antibody. Specifically, it has been found by the present inventors that the humans for supplying the lymphocyte cells should have high antibody titers of anti-HBsAg. Thus, such lymphocyte cells can be derived from humans who once have relatively high titers of anti-HBs (for example, at least 0.1 IU/ml) due to possible infections with hepatitis B virus in the past and are then administered with an HBs vaccine so that their titers of anti-HBsAg develop to at least 10 IU/ml (preferably at least 100 IU/ml) in blood two to three weeks after the vaccination. Alternatively, the second selection may be carried out by selecting out humans whose peripheral blood lymphocyte cells are collected after the administration of the HBs vaccine and then cultured in vitro so that the culture supernatant contains anti-HBsAg antibody of at least 0.01 IU/ml (preferably at least 0.1 IU/ml). The peripheral blood lymphocyte cells collected two to three weeks after the vaccination are then cultured in vitro, where there is employed a lymphocyte activating substance such as pokeweed mitogen (PWM). The use of peripheral blood lymphocyte cells derived from humans who show negativity for titer of anti-HBsAg in blood before the vaccination or humans who have the high antibody titers as defined makes it extremely difficult to form mouse/human hybridomas which are capable of producing the desired hHBs MCA.

The human peripheral blood lymphocyte cells thus cultured are collected to be used for forming mouse/human hybridomas by being fused with mouse myeloma cells (X63-Ag8-6,5,3 or other cells derived from the MOPC-21 line). The cell fusion can be carried out in any known manner with a fusing agent exemplified by polyethyleneglycol. The selection of hybridomas is accomplished by culturing in a suitable medium, particularly in HAT (hypoxanthine-aminopterin-thymidine) selective medium, for example, in RPM 1640+15% fetal bovine serum+HAT medium added with glutamine, at 37° C. in the presence of 5% $CO_2$. The hybridomas which will produce anti-HBsAg antibodies are confirmed by means of such method as passive hemagglutination (PHA) using sheep red blood cells sensitized with HBs antigen, conventional antibody-determining methods for IgG or IgM, or radioimmunoassay.

The mouse/human hybridomas which produce anti-HBsAg antibodies thus selected are subjected to cloning operation by means of limiting dilution so as to be established as monoclones for producing the human-based anti-HBsAg monoclonal antibodies, in which for establishing antibody-producing stable clones it is essential to repeatedly carry out such cloning operations at early stages.

The hHBs MCA-producing mouse/human hybridomas as established in the above-mentioned manner are then propagated in vitro or in an immunodeficient animal so as to continuously produce the MCA to HBsAg. For example, in a case where pristane-primed nude mice derived from BALB/c were intraperitoneally administered with the clones and, three to five weeks after the administration, were determined by RIA with respect to anti-HBsAg antibody in the ascites, there was obtained antibody specific for HBsAg from three of seven mice. Alternatively, the hybridoma cells can be propagated in vitro, particularly in a medium containing hypoxanthine-aminopterin-thymidine. The propagated hHBs MCA are then recovered (purified) in a known manner as applied to recover immunoglobulin, for example, by conventional salting-out, DEAE-ion exchange chromatography, polyethyleneglycol-fractionation, gel filtration, affinity chromatography with HBsAg-fixed beads or the like, from the supernatants of the cultures for the hybridomas or the ascites fluid of the nude mice. If necessary, there may be employed treatments which are known in the production of immunoglobulin for intravenous injection, such as acid treatment, enzyme treatment, plasmin treatment, sulfonating treatment or polyethyleneglycol treatment. For pharmaceutical preparation, the purified anti-HBsAg monoclonal antibody undergoes known process, which may include concentration conditioning, addition of stabilizer(s), bacterial filtration and lyophilization.

It is evidenced that the anti-HBsAg monoclonal antibody produced by the mouse/human bybridoma according to the present invention is complete human IgG antibody in the immunoglobulin class, not a human/mouse chimeric antibody. When determined by immune precipitation method, it is found the monoclonal antibody of the present invention forms a precipitate with rabbit anti-human IgG antiserum but forms no precipitate with rabbit anti-mouse IgG antiserum. In addition, analysis by radioimmunoassay, which is more sensitive than immune precipitation, shows that the MCA according to the present invention reacts with radioactively-labelled rabbit anti-human IgG in proportion to the concentration of the antibody, but no reaction takes place with radioactively-labelled rabbit anti-mouse IgG.

Furthermore, as a result of test by means of PHA (passive hemagglutination)-inhibition employing sheep red blood cells sensitized with HBs antigen, it has been evidenced that the hHBs MCA according to the present invention is an antibody which recognizes or identifies the epitope "a", i.e. the antigenic determinant common to all the subclasses of HBs antigen. As is known, HBs antigen can be classified into four subclasses (adw, adr, ayw, and ayr) because of the presence of one common epitope (a) and two divided pairs of epitopes (d, y) and (w, r). The present invention is of a great significance since it provides a monoclonal antibody being capable of recognizing the epitope (a) and hence reacting with all the types of hepatitis B surface antigen.

The hybridoma formed by the present invention, when cultured in vitro, is found to be able to produce the L antibody specific for HBsAg in an amount of 7 $\mu$g/ml (7 $\mu$g/$5\times10^5$ cells/ml), where the antibody titer is $2^{12}$ in terms of PHA or 50 IU (International Unit)/ml. These values demonstrate that the hybridoma is of a practical usefulness. It is also found that the hybridoma exhibits a doubling time of thirty hours and contains the fourteenth chromosome when determined by Q-band staining technique. The hybridoma of the present invention can be cultured without causing any substantial change, at least one year according to the finding by the inventors, to produce the hHBs MCA continuously and stably.

Thus, the method of the present invention can be carried out in a relatively simple manner without need of complicated stages to prepare the hHBs MCA which has wide applications such as those in the diagnosis or the treatment of hapatic diseases or in the purification of HBs antigen.

The present invention is illustrated by the following example, which is not intended to limit the invention.

EXAMPLE

1. Preparation of immunizing antigen (vaccine):

Step 1: Anti-HBs antibody-positive human plasma was treated with calcium chloride and dextran sulfate, followed by salting-out of the supernatant with 1.2 M ammonium sulfate. After centrifugation, there was added to the supernatant with 1.8 M ammonium sulfate so as to precipitate the HBs antigen. Thus, there were removed about 80% of the human plasma components and the plasma was concentrated about ten times.

Step 2: DEAE-Sepharose GL-6B gel (available from Pharmacia Co..) was sufficiently equilibrated with acetate buffer having ionic strength 0.05 and pH 5.5 and then packed within a column. After the HBs antigen-containing solution as obtained in Step 1 was subjected to dialysis with the above-mentioned buffer and the precipitate formed by dialysis was removed by centrifugation, the resultant solution was passed through the column. Thus, elution was carried out in the manner of changing ionic strength stepwise with sodium chloride.

There was recovered 80% of the HBs antigen in the passed-through fraction, in which primary serum protein was $\gamma$-globulin. The degree of purification was found to be fourteen times as compared with the starting material.

Step 3: CM-Sepharose CL-6B (available from Pharmacia Co.) gel was packed into a column after sufficient equilibration with acetate buffer having ionic strength 0.08 and pH 5.1. The passed-through fraction obtained in Step 2 was subjected to dialysis with the buffer and passed through the column. The elution operation was carried out stepwise with sodium chloride. There was recovered 24 to 48% of the HBs antigen as the passed-through fraction, where the HBs antigen was found to have been further purified to 1,500 times as high as the starting material.

The final fraction contained the HBs antigen in terms of 1,024 as determined by $\gamma$-PHA. Analysis by Kjeldahl method showed that it contained proteins of 6 $\mu$g/ml. There were detected no serum components when the fraction, concentrated to 10 to 100 times, was analyzed by immunodiffusion or immunoelectrophoresis. Examination of the serum proteins of rabbits, highly immunized with the purified HBs. antigen, showed that there were four weak precipitation lines against NHS (normal human serum).

2. Selection of lymphocyte cells-supplying humans and immunization:

Selection is firstly made of humans who have high antibody titers of anti-HBs antigen (at least 0.1 IU/ml) in blood, by means of PHA or radioimmunoassay. Then, each of the selected humans is subcutaneously administered with 20 $\mu$g of the HBs vaccine as prepared in the above-mentioned manner and, about 2 weeks after the administration, there are selected humans who have titers of anti-HBs antigen of at least 10 IU/ml (most preferably at least 100 IU/ml) in blood. The second selection may also be carried out by selecting out humans whose peripheral blood lymphocyte cells are collected after the administration of the HBs vaccine and then cultured in vitro so that the culture supernatant contains a significant amount of anti-HBsAg antibody, i.e. at least 0.01 IU/ml, preferably at least 0.1 IU/ml.

3. Preparation of human peripheral blood lymphocyte cells:

From peripheral blood collected at a predetermined time after the vaccine administration, peripheral blood lymphocyte cells were harvested by Ficol-Hypaque gradient centrifugation of the peripheral blood. The lymphocyte cells were then suspended at $1 \times 10^6$ cells/ml in RPMI 1640+15% bovine fetal serum added with glutamine followed by the addition of PWM at 2.5 the final concentration of $\mu$g/ml. Following culturing at 37° C. in the presence of $CO_2$ for 4 to 5 days, the production of anti-HBsAg antibody was detected in the culture supernatant. The lymphocyte cells were collected, washed twice with RPMI 1640 medium and then resuspended in the medium. The peripheral blood lymphocyte cells were obtained generally at a rate of about $4 \times 10^7$ cells from 40 ml of the peripheral blood, half of which ($2 \times 10^7$ cells were subjected directly to cell fusion with mouse myeloma cells to study the effects of the stimulation by PWM on the cell fusion as described later, with the remaining being supplied to cell fusion with the PWM stimulation.

4. Preparation of Myeloma cells:

The myeloma cell line used in the present invention was derived from mouse BALB/c myeloma as known from the disclosures in "Nature, 256, pp. 495-497 (1975)" or Eur. J. Immunol., 6, pp. 511-519 (1976)" by Kohler et al, particularly X63-Ag8-6,5,3 or P3-X63-Ag8-U1. The myeloma cells were propagated in complete medium of RPMI 1640+15% bovine fetal serum added with glutamine. The propagated cells were collected, washed twice with RPMI medium and then resuspended in the medium for use in the cell fusion.

5. Cell fusion between human peripheral blood lymphocyte cells and mouse myeloma cells:

The human lymphocyte cells suspension was mixed with the mouse myeloma cells suspension at a ratio of the human lymphocyte cells: the mouse myeloma cells=1:2 and the mixture was centrifuged for 10 minutes at a rate of 1,500 rpm to form a pellet, to which was added, over one minute at 37° C., 1 ml of 45% polyethyleneglycol solution (pH 7.6, molecular weight 3,650) diluted with RPMI 1640. The resultant mixture, after being allowed to stand for five minutes, was added with 40 ml of RPMI 1640 and the cells were gently resuspended to terminate the fusion. Then the cells were subjected to centrifugation for 10 minutes at a rate of 1,000 rpm and resuspended in complete medium containing RPMI 1640+15% bovine fetal serum added with glutamine to obtain fused cells at a human lymphocyte cell concentration of $5 \times 10^5$ cells/ml and at a myeloma cell concentration of $1 \times 10^6$ cells/ml. The resultant cells were plated in 96-well microtiter plates at a ration of 100 $\mu$l per one well, followed by culturing at 37° C. in the presence of 5% $CO_2$. After 24 hours, to each well was added 100 $\mu$l of HAT selective medium (RPMI 1640+15% bovine fetal serum+HAT added with glutamine). Further, at times of 24 hours and 48 hours later, 50% of medium in each well was replaced with the HAT selective medium. Such 50% medium replacements with the selective HAT medium were subsequently conducted every five days for two to three weeks until the hybridomas were sufficiently propagated for screening assay.

6. Screening assay and cloning of hybridomas:

For confirming sufficient propagation of the hybridomas, screening assay was carried out to detect clones producing the specific antibody: Firstly were screened the wells in which there was produced any antibody by means of radioimmunoassay (for determining human antibody), and then there were screened, by means of radioimmunoassay for detecting anti-HBsAg antibody known as AUSAB ® (Anti-HBsAg detecting kit available from Dinabot Co.), the wells in which there was produced antibody specific for HBsAg. The hybridomas in the wells thus screened were subjected to limiting dilution for cloning. At the time when the clones were propagated in the wells, the radioimmunoassay was effected to detect clones producing antibody specific for HBsAg. Such operations were repeatedly carried out as required to obtain stable mouse/human hybridomas. Depending upon necessities the hybridomas were propagated and stored in a frozen state under liquid nitrogen in freezing medium of HAT selective medium+10% DMSO (dimethylsulfoxide).

7. Effect of vaccine administration:

As shown in Table 1, the human peripheral blood lymphocyte cells for forming the hHBs MCA-producing hybridomas according to the present invention were derived from selected humans who had relatively high titers of anti-HBsAg (at least 0.1 IU/ml) in blood due to possible infections with hepatitis B virus in the past.

Such persons were then administered with the HBs vaccine and, two weeks after the vaccination, were determined for their antibody titers of anti-HBsAg. The results were also given in Table 1, demonstrating that hybridomas which effectively produce anti-HBsAg antibody were derived from humans who exhibited high titers in blood after the vaccine administration, i.e. at least about 10 IU/ml, most preferably at least about 100 IU/ml.

TABLE 1

| Lympho-cyto Suppliers | Anti-HBsAg Titer before vaccine Administration (IU/ml) | Anti-HBsAg Titer after vaccine Administration (IU/ml) | Rate of Formation of anti-HBsAg Producing Hybridomas (%) | |
|---|---|---|---|---|
| | | | Exp. 1 | Exp. 2 |
| A | 0.8 | 2.7 | 0 | 0 |
| B | 0.7 | 3.6 | 0 | 0 |
| C | 0.2 | 1.3 | 0 | 0 |
| D | 0.1 | 15.5 | 1 | 0 |
| E | 14.0 | 443.5 | 12 | 9 |
| F | 0.9 | 174.2 | 10 | 6 |
| G | 3.0 | 124.8 | 7 | 3 |
| H | 6.2 | 315.7 | 7 | 6 |

(Note)
(1) The International Unit (IU/ml) were determined by AUSAB ®
(2) Rate of Formation of Anti-HBsAg-Producing Hybridomas (%) = (The number of wells in which anti-HBsAg were produced/The total number of wells in which hybridomas are formed) × 100

Alternatively, hybridomas which effectively product anti-HBsAg antibody can be derived from humans whose peripheral blood lymphocyte cells are cultured, after the vaccine administration, in vitro so that the culture supernatants exhibit high titers of anti-HBsAg. Thus, the peripheral lymphocyte cells of the suppliers were collected, one week after the vaccine administration, and cultured in complete medium of RPMI 1640+15% bovine fetal serum added with glutamine at 37° C. in the presence of 5% $CO_2$ for seven days. The culture supernatants were determined with respect to titers of anti-HBsAg. The results are summarized in Table 2, which demonstrates that, for obtaining the hybridomas effectively producing anti-HBsAg antibody, the culture supernatants should have the titers of at least 0.01 IU/ml, most preferably at least about 0.1 IU/ml.

TABLE 2

| Lympho-cyto Suppliers | Culture Supernatant Titer (IU/ml) | | Rate of Formation of anti-HBsAg Producing Hybridomas (%) | |
|---|---|---|---|---|
| | Before Immunization | One Week After Immunization | Exp. 1 | Expo 2 |
| A | ND | ND | 0 | 0 |
| B | ND | ND | 0 | 0 |
| C | ND | ND | 0 | 0 |
| D | ND | 0.01 | 1 | 0 |
| E | ND | 0.8 | 12 | 9 |
| F | ND | 0.3 | 10 | 6 |
| G | ND | 0.2 | 7 | 3 |
| H | ND | 0.8 | 7 | 6 |

(Note) ND: No Anti-HBsAg antibody was detected.

8. Effects of lymphocyte cells collection timing and addition of pokeweed mitogen:

FIG. 1 illustrates the rate of formation of anti-HBsAg-producing hybridomas against time (one week, two weeks and three weeks) lapsed after the vaccine administration, with respect to some of the suppliers. As seen from FIG. 1, the lymphocyte cells collected two weeks after the vaccine administration will most efficiently form the desired hybridoma.

FIG. 1 also gives the results of the cases where PWM (pokeweed mitogen) were added prior to the cell fusions (shown in solid bars) and the cases where no PWM were added (shown in blank bars). It should be noted that, in the cases in which there present no bars in the graphs, no hybridomas were formed. The results demonstrate that addition of a lymphocyte activator such as PWM is very effective in forming the hybridoma.

9. Characterization of the hybridoma:

It was confirmed by means of conventional antibody-determining technique that the hybridoma according to the present invention when cultured in HAT medium produces anti-HBsAg antibody at the rate of 7 $\mu g/5 \times 10^5$ cells/ml. The titer of the specific antibody is $2^{12}$ in terms of PHA as determined by hemagglutination method employing sheep red blood cells sensitized with HBsAg, and 50 in terms of IU/ml. These values substantially correspond to those found in humans having high titers of anti-HBsAg in blood.

The anti-HBsAg monoclonal antibody prepared by the present invention does not react at all with anti-mouse immunoglobulin antiserum but reacts only with anti-human IgG antiserum, from which it is evidenced that the monoclonal antibody of the present invention belongs to the immunoglobulin class of human IgG.

The specificity of the monoclonal antibody of the present invention was determined by PHA-inhibition test employing sheep red blood cells sensitized with HBsAg, with the results as shown in Table 3.

TABLE 3

| Monoclonal Antibody | HBsAg | | | Epitope recognized |
|---|---|---|---|---|
| | adr | adw | ayw | |
| Human MCA (the present invention) | >32 | 32 | >32 | a |
| Mouse MCA HB7-2 | >32 | >32 | >32 | a |
| Mouse MCA HB6-2 | 16 | >32 | <2 | a |
| Mouse MCA HB5-2 | 8 | <2 | <2 | r |

(Note) The numerical values in the table are dilution factors.

For comparison, the test was also conducted on some mouse monoclonal antibodies(MCA), the specificities of which were known in advance.

As a result, the hHBs MCA prepared according to the present invention reacted with all the subtypes, adr, adw, and ayw, of HBs antigen without causing hemagglutination. It was also found that the human anti-HBsAg monoclonal antibody of the present invention exhibited a reaction pattern quite similar to the pattern of the mouse MCA (designated HB7-2) which is known to recognize epitope "a" on HBs antigen. From these facts it was evidenced that the monoclonal antibody of the present will react with all the subtypes of hepatitis B surface antigen, suggesting that the monoclonal antibody of the invention is quite effective in preventing and treating the diseases due to the infection of hepatitis B virus.

Figure 2:
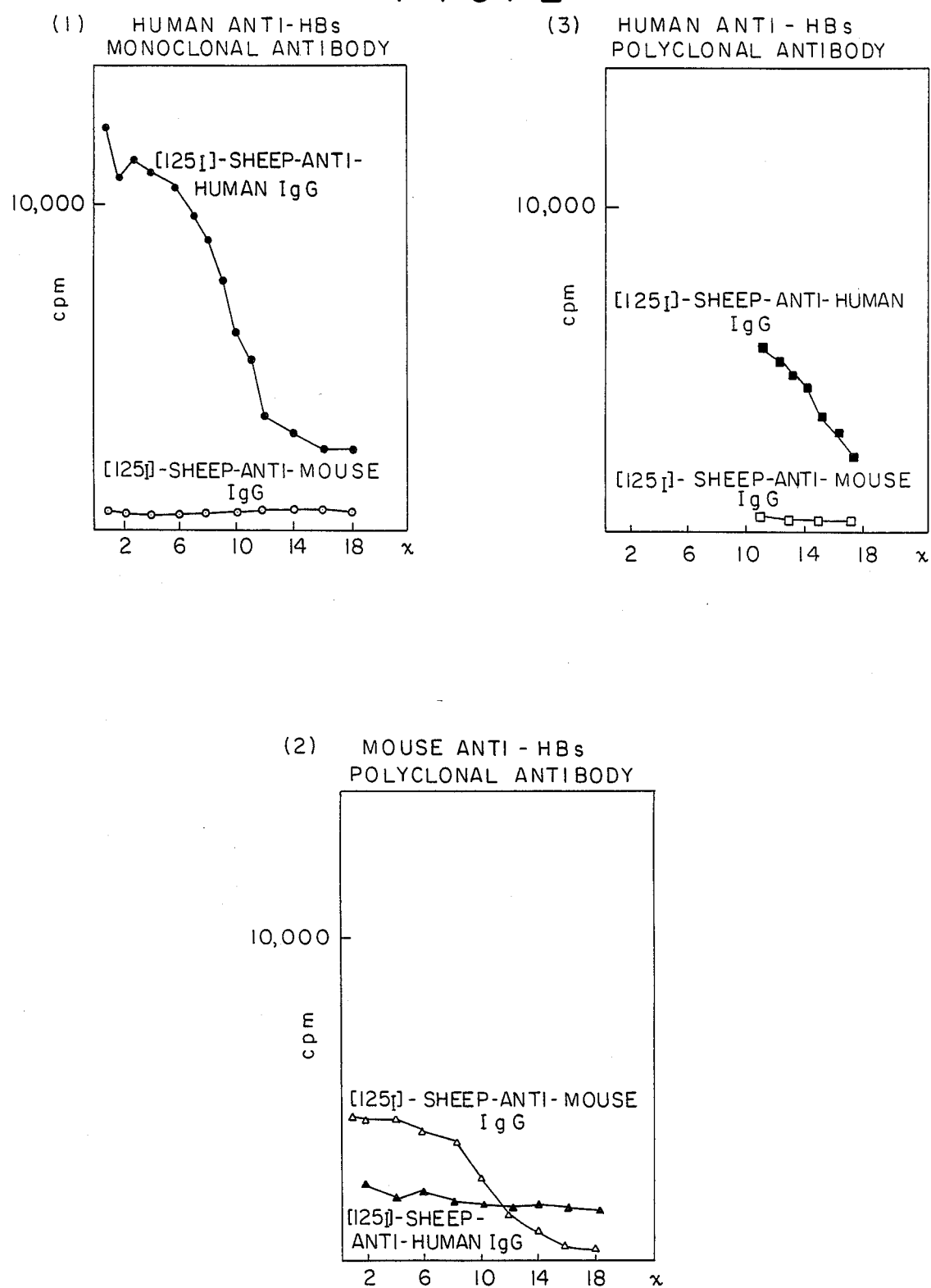

FIG. 2 illustrates the results of the reaction of the human monoclonal antibody of the present invention, which has been bound onto HBsAg-sensitized polystyrene beads, with [$^{125}$I]-sheep-anti-human IgG or [$^{125}$I]-sheep-anti-mouse IgG. The results are also given with respect to a human anti-HBsAg polyclonal antibody (derived from human serum) and the mouse anti-HBsAg monoclonal antibody, as controls. In the graphs of FIG. 2, the abscissas designate dilution factors (in terms of x in $\frac{1}{2}^x$) of the anti-HBs antibodies with the ordinates indicating cpm (counts per minute) as determined by the radioimmunoassay.

The human monoclonal antibody of the present invention does not react at all with [$^{125}$I]-sheep-anti-mouse IgG but reacts remarkably with [$^{125}$I]-sheep-anti-human IgG substantially linearly with the concentration of the antibody as seen from FIG. 2. The human anti-HBsAg polyclonal antibody derived from human serum exhibited a reaction pattern quite similar to that of the monoclonal antibody of the present invention while the mouse anti-HBsAg monoclonal antibody (HB7-2) exhibited a definitely different reaction pattern. From these facts, it is believed that the anti-HBsAg monoclonal antibody prepared by the present invention is a complete human antibody, not a human/mouse chimeric antibody.

What is claimed is:

1. A method for preparing a human-derived monoclonal antibody to hepatitis B surface antigen (HBsAg) comprising the steps of:
    administering HBsAg vaccine to humans who test positive with respect to anti-HBsAg antibody;
    recovering lymphocyte cells from the humans having a titer of anti-HBsAg of at least 10 IU/ml in blood two weeks after administration of said HBsAg;
    culturing the lymphocyte cells in vitro for seven days and selecting the lymphocyte cells with a culture supernatant containing anti-HBsAg antibody in an amount of at least 0.01 IU/ml;
    stimulating the lymphocyte cells by addition of a non-specific lymphocyte activator;
    fusing the lymphocyte cells to myeloma cells to form hybridomas;
    cloning said hybridomas;
    selecting clones producing the antibody to HBsAg; and
    culturing said hybridomas and collecting the antibody to HBsAg produced by said hybridomas.

2. The method as claimed in claim 1, wherein lymphocyte cells are recovered from the humans having a titer of anti-HBsAg of at least 100 IU/ml in blood two weeks after administration of said HBsAg.

3. The method as claimed in claim 1, wherein the culture supernatant contains anti-HBsAg antibody in an amount of at least 0.2 IU/ml.

4. The method as claimed in claim 1, wherein the non-specific lymphocyte activator is pokeweed mitogen.

5. The method as claimed in claim 1 wherein the myeloma cells are derived from mouse BALB/c myeloma cells, particularly P3-X63-Ag8-U1 or X-63-Ag8-6,5,3.

6. The method as claimed in claim 1, wherein the hybridomas are cultured in vitro.

7. The method as claimed in claim 1 wherein the hybridomas are propagated in an immunodeficient animal.

8. The method as claimed in claim 5, wherein the hybridomas are culturing in a medium containing hypoxanthine-aminopterin-thymidine.

* * * * *